United States Patent
Smith, III et al.

(10) Patent No.: US 7,709,654 B2
(45) Date of Patent: May 4, 2010

(54) PROCESS FOR PRODUCING OXAZOLE, IMIDAZOLE, PYRRAZOLE BORYL COMPOUNDS

(75) Inventors: Milton R. Smith, III, East Lansing, MI (US); Robert E. Maleczka, Jr., DeWitt, MI (US); Venkata A. Kallepalli, East Lansing, MI (US); Edith Onyeozili, Tallahassee, FL (US)

(73) Assignee: Board of Trustees of Michigan State University, East Lansing, MI (US)

( * ) Notice: Subject to any disclaimer, the term of this patent is extended or adjusted under 35 U.S.C. 154(b) by 20 days.

(21) Appl. No.: 11/900,329

(22) Filed: Sep. 11, 2007

(65) Prior Publication Data

US 2008/0091027 A1    Apr. 17, 2008

Related U.S. Application Data

(60) Provisional application No. 60/843,589, filed on Sep. 11, 2006.

(51) Int. Cl.
*C07D 263/30* (2006.01)
*C07D 263/34* (2006.01)
*C07D 233/54* (2006.01)
*C07D 233/68* (2006.01)
*C07D 231/10* (2006.01)
*C07D 231/16* (2006.01)

(52) U.S. Cl. ........... 548/235; 548/335.1; 548/343.1; 548/343.3; 548/346.1; 548/373.1

(58) Field of Classification Search ........... 548/235, 548/335.1, 373.1
See application file for complete search history.

(56) References Cited

U.S. PATENT DOCUMENTS

2005/0148775 A1    7/2005    Miyaura et al.

2008/0091035 A1    4/2008    Smith et al.
2008/0146814 A1    6/2008    Smith et al.
2008/0167476 A1    7/2008    Smith et al.

FOREIGN PATENT DOCUMENTS

WO    WO 03/006158 A2 *    1/2003

OTHER PUBLICATIONS

Ishiyama et al., Iridium-Catalyzed Direct Borylation of Five-Membered Heteroarenes by Bis(pinacolato)diboron: Regioselective, Stoichiometric, and Room Temperature Reactions, 2003, Adv. Synth. Catal., 345, 1103-1106.*
Takagi et al., Iridium-catalyzed C-H coupling reaction of heteroaromatic compounds with bis(pinacolato)diboron: regioselective synthesis of heteroarylboronates, 2002, Tetrahedron Letters, 43, 5649-5651.*
Ivachtchenko et al., Synthesis of Pinacol Esters of 1-Alkyl-1H-pyrazol-5-yl- and 1-Alkyl-1H-pyrazol-4-ylboronic Acids, 2004, J. Heterocyclic Chem., 41, 931-939.*
Romero, F.A.; Du, W.; Hwang, I.; Rayl, T.J.; Kimball, F.S.; Leung, D.; Hoover, H.S.; Apodaca, R.L.; Breitenbucher, J.G.; Cravatt, B.F.; Boger, D.L., J. Med. Chem. 2007, 50, 1058-1068.
Hashimoto, H.; Imamura, K.; Haruta, J.; Wakitani, K., J. Med. Chem. 2002, 45, 1511-1517.
Harris, P.A.; Cheung, M.; Hunter, R.N., III; Brown, M.L.; Veal, J.M.; Notle, R.T.; Want, L.; Liu, W.; Crosby, R.M.; Johnson, J.H.; Epperly, A.H.; Kumar, R.; Luttrell, D.K.; Stafford, J.A., J. Med. Chem. 2005, 48, 1610-1619.
Brown, P.; Davies, D.T.; O'Hanlon, P.J.; Wilson, J.M., J. Med. Chem. 1996, 39, 446-457.
Razavi, H.; Powers, E.T.; Purkey, H.E.; Adamski-Werner, S.L.; Chiang, K.P.; Dendle, M.T.A.; Kelly, Jeffery W., Bioorg. Med. Chem. Lett. 2005, 15, 1075-1078.

* cited by examiner

*Primary Examiner*—Kamal A Saeed
*Assistant Examiner*—Kristin Bianchi
(74) *Attorney, Agent, or Firm*—Ian C. McLeod; Steven M. Parks

(57) ABSTRACT

Process for the preparation of oxazole, imidazole, and pyraxole boryl compounds. The compounds are intermediates to functionalized compounds, both natural and synthetic which are cytotoxic, anticancer and antiviral agents.

20 Claims, No Drawings

US 7,709,654 B2

PROCESS FOR PRODUCING OXAZOLE, IMIDAZOLE, PYRRAZOLE BORYL COMPOUNDS

CROSS-REFERENCE TO RELATED APPLICATIONS

This application claims benefit to U.S. Provisional Application Ser. No. 60/843,589, filed Sep. 11, 2006, which is incorporated herein by reference in its entirety.

STATEMENT REGARDING FEDERALLY SPONSORED RESEARCH OR DEVELOPMENT

This work was supported by a grant from the National Institute of Health (NIH)—Grant No. GM063188. The U.S. Government has certain rights to this invention.

BACKGROUND OF THE INVENTION (1) Field of the Invention

The present invention relates to the preparation of oxazole, imidazole, and pyrazole boryl compounds, using iridium complexes. The present invention also relates to novel compounds.

(2) Description of the Related Art

Oxazoles have a wide variety of applications in synthetic organic chemistry and have been found in numerous natural products such as hennoxazole, thiangazole, calyculin, halicondrins, pyrenolide, virginiamycin, amphotericin, and phorboxazoles.[a] New studies have illustrated the particular utility of 5-substituted oxazoles. For example, a very recent structure-activity relationship study targeting the 5-position of an oxazole based inhibitor of fatty acid amide hydrolase (FAAH) revealed that the optimal position for substitution was the meta-position. Concurrent with these studies, a series of small, nonaromatic C5-substituents was also explored and revealed that the Ki follows a well-defined correlation with the Hammett p constant (=3.01, R2=0.91) in which electron-withdrawing substituents enhance potency, leading to inhibitors with K is as low as 400 pM (20n). Proteomic-wide screening of theses inhibitors revealed that most are exquisitely selective for FAAH over all other mammalian proteases.[b] In another investigation, a series of 4-(4-cycloalkyl/aryl-oxazol-5-yl)benzenesulfonamide derivatives were synthesized and evaluated for their abilities to inhibit cyclooxygenase-2 (COX-2) and cyclooxygenase-1 (COX-1) enzymes. This work led to the identification of a potent, highly selective, and orally active COX-2 inhibitor JTE-522 [4-(4-cyclohexyl-2-methyloxazol-5-yl)-2-fluorobenzene-sulfonamide], which is currently in phase II clinical trials for the treatment of rheumatoid arthritis, osteoarthritis, and acute pain.[c] 2-Anilino-5-phenyloxazoles have also been identified as inhibitors of VEGFR2 kinase. In this case, optimization of both aryl rings led to very potent inhibitors at both the enzymatic and cellular levels. These oxazole-based compounds had excellent solubility and good oral PK when dosed as the bis-mesylate salt and demonstrated in vivo efficacy against HT29 human colon tumor xenografts. Furthermore substitution at the 5-position proved especially instructive as X-ray crystallography confirmed the proposed binding mode and revealed interesting differences in orientation of 2-pyridyl and 3-pyridyl rings, respectively, attached at the meta position of the 5-phenyl ring.[d] In yet another report, the antibacterial activity of a range of 5-alkyl, 5-alkenyl, and 5-heterosubstituted 2-(1-normon-2-yl) oxazoles against a range of Gram-positive and Gram-negative organisms demonstrated the importance of substitution on potency. Compounds possessing an acid functionality directly on, or close to, the ring were found to be of greatly decreased potency, while increasing lipophilicity with greater chain length led to increased potency of these derivatives.[e] Likewise, in the search for transthyretin (TTR) amyloid fibril inhibitors, oxazoles bearing a C(4) carboxyl group and various aryls at the C(2) position of the oxazole ring reveals that a 3,5-dichlorophenyl substituent significantly reduced amyloidogenesis. The efficacy of these inhibitors was enhanced further by installing an ethyl, a propyl, or a $CF_3$ group at the C(5) position. The $CF_3$ substitution at C(5) also improves the TTR binding selectivity over all the other proteins in human blood.[f]

OBJECTS

These and other objects will become increasingly apparent by reference to the following description and drawings.

SUMMARY OF THE INVENTION

The present invention provides a process for producing an oxazole (I), imidazole (II), or pyrazole (III) boryl compound wherein $R_1$ is selected from the group consisting of hydrogen, boryl, halo, cyano, alkyl, alkoxy, thioalkyl, amino alkyl, acyl, alkyl aminoacyl, trifluoro alkyl, aryl, alkyl silyl, and containing 1 to 8 carbon atoms except for the halo group and boryl group, wherein $R_2$ is selected from the group consisting of methyl, isopropyl, triisopropylsilyl, phenyl, benzyl, para-methoxybenzyl, tert-butoxycarbonyl, (benzyloxy)carbonyl, N,N-dimethylaminosulfonyl, N,N-dimethylcarboxamide, para-toluenesulfonyl, 9H-Fluoren-9-ylmethyloxycarbonyl, and other common nitrogen protecting groups,

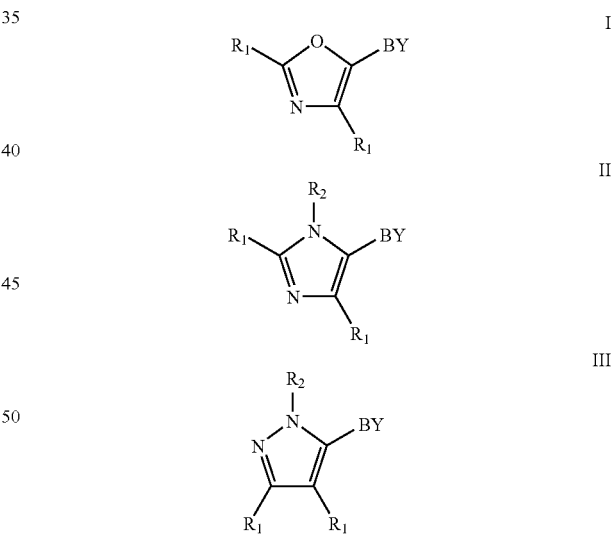

which comprises: reacting an oxazole (IV), imidazole (V), or pyrazole (VI) wherein $R_1$ is selected from the group consisting of hydrogen, boryl, halo, cyano, alkyl, alkoxy, thioalkyl, amino alkyl, acyl, alkyl aminoacyl, trifluoro alkyl, aryl, alkyl silyl, and containing 1 to 8 carbon atoms except for the halo group and boryl group, wherein $R_2$ is selected from the group consisting of methyl, isopropyl, triisopropylsilyl, phenyl, benzyl, para-methoxybenzyl, tert-butoxycarbonyl, (benzyloxy)carbonyl, N,N-dimethylaminosulfonyl, N,N-dimethylcarboxamide, para-toluenesulfonyl, 9H-Fluoren-9-ylmethyloxycarbonyl, and other common nitrogen protecting groups,

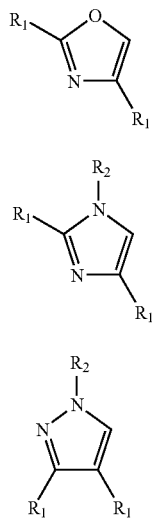

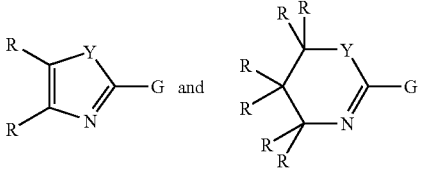

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and G is a heteroatom containing group, multiple atom chain, or multiple atom ring. In still further embodiments, the complex is an iridium complex of [Ir(OMe)(COD)]$_2$, [Ir(Cl)(COD)]$_2$, or (COD) ($\eta^5$-indenyl)Ir, where COD is 1,5-cyclooctadine, complexed with a ligand selected from the group consisting of:

in a reaction mixture with a non-reactive solvent selected from, but not limited to, aliphatic hydrocarbons and ethers at temperatures between about 0 and 150° C. with an HB or B—B organic compound, in the presence of a catalytically effective amount of an iridium complex catalytic composition comprising an iridium complex of the formula: (BY)$_n$-Ir-(ligand)$_m$ where n is equal to one to five and m is equal to one to three, excluding hydrogen, bonded to the indium BY is a boron moiety and the ligand is selected from the group consisting of a phosphorus organic ligand, an organic amine, an imine, a nitrogen heterocycle, and an ether wherein the ligand is at least in part bonded to the iridium, to form the compounds (I-III) in the reaction mixture; and evaporating the solvent and portions of the reaction mixture which are volatile from the reaction mixture to produce the compound (I-III).

The present invention provides an oxazole (I), imidazole (II), or pyrazole (III) boryl compound wherein R$_1$ is selected from the group consisting of hydrogen, boryl, halo, cyano, alkyl, alkoxy, thioalkyl, amino alkyl, acyl, alkyl aminoacyl, trifluoro alkyl, aryl, alkyl silyl, and containing 1 to 8 carbon atoms except for the halo group and boryl group, wherein R$_2$ is selected from the group consisting of methyl, benzyl, para-methoxybenzyl, tert-butoxycarbonyl, (benzyloxy)carbonyl, N,N-dimethylaminosulfonyl, N,N-dimethylcarboxamide, para-toluenesulfonyl, 9H-Fluoren-9-ylmethyloxycarbonyl, and other common nitrogen protecting groups. In further embodiments, the complex is an iridium complex of [Ir(OMe)(COD)]$_2$, [Ir(Cl)(COD)]$_2$, or (COD) ($\eta^5$-indenyl)Ir, where COD is 1,5-cyclooctadine, complexed with a ligand selected from the group consisting of:

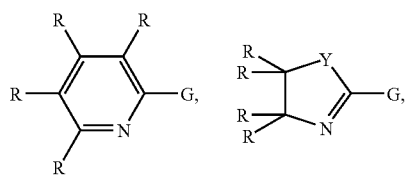

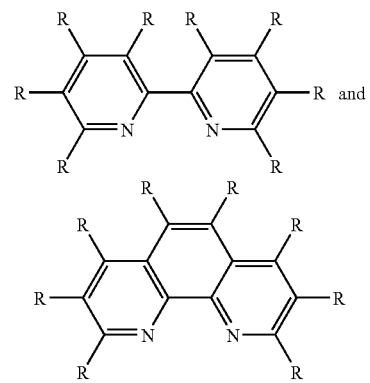

wherein R are each selected from the group consisting of hydrogen, linear alkyl containing 1 to 8 carbon atoms, branched alkyl containing 1 to 8 carbons, and a carbon in a cyclic structure. In further still embodiments, the complex is an iridium complex of [Ir(OMe)(COD)]$_2$, [Ir(Cl)(COD)]$_2$, or (COD) ($\eta^5$-indenyl)Ir, where COD is 1,5-cyclooctadine, complexed with a ligand selected from the group consisting of:

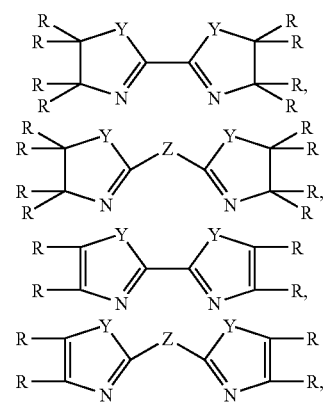

-continued

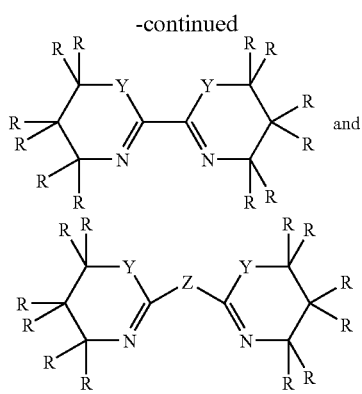

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and Z is a carbon, oxygen, nitrogen, sulfur, or boron containing moiety or a multiple atom chain containing a carbon, oxygen, nitrogen, sulfur, or boron containing moiety. In still further embodiments, the complex is an iridium complex of $[Ir(OMe)(COD)]_2$, $[Ir(Cl)(COD)]_2$, or (COD) ($\eta^5$-indenyl)Ir, where COD is 1,5-cyclooctadine, complexed with a ligand selected from the group consisting of:

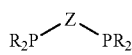

wherein R are each selected from the group consisting of hydrogen, aryl, linear alkyl containing 1 to 8 carbon atoms, branched alkyl containing 1 to 8 carbons, alkoxy, or a carbon in a cyclic structure and Z is a carbon, oxygen, or nitrogen containing moiety or a multiple atom chain containing a carbon, oxygen, or nitrogen containing moiety. In further still embodiments, the HB or B—B organic compound is HBPin or $B_2Pin_2$. In still further embodiments, the complex is an iridium complex of $[Ir(OMe)(COD)]_2$, $[Ir(Cl)(COD)]_2$, or (COD)($\eta^5$-indenyl)Ir, where COD is 1,5-cyclooctadine, complexed with 4,4-di-t-butyl-2,2'bipyridine (dtbpy). In further still embodiments, the complex is an iridium complex of $[Ir(OMe)(COD)]_2$, $[Ir(Cl)(COD)]_2$, or (COD) ($\eta^5$-indenyl)Ir, where COD is 1,5-cyclooctadine, complexed with 1,2-bis(dimethylphospino)ethane.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

General Procedure A

In a dry glove box, an air-free flask, equipped with a magnetic stirring bar, is charged with [Ir(OMe)(COD)]2 (9.9 mg, 0.015 mmol, 3 mol % Ir), excess HBPin (typically, 1.5 equivs for monoborylation and 2.5), and pentane (typically 1.0 mL) and the mixture stirred at room temperature for 10 to 15 min. Then dtbpy (8.1 mg, 0.03 mmol, 3 mol %) is added to this mixture (with rinse with 0.5-1.0 mL) and reaction stirred for additional 20 min. The heteroaryl substrate (1 mmol, 1.0 equiv) is dissolved in pentane, THF or ether (typically 1-1.5 mL) and added to the active catalyst mixture. The reaction is stirred at room temperature until complete (monitored by TLC and GC-FID). Solvent is removed under reduced pressure, and the crude material is washed with pentane (3 mL portions until wash is colorless) to furnish the desired borylated product. Analytically pure sample is obtained by kuegelrohr distillation and used for spectroscopic and elemental analyses.

General Procedure B

In a glove box, a Schlenk flask, equipped with a magnetic stirring bar, was charged with the corresponding heteroaryl compound (1 mmol, 1 equivalent), (Ind)Ir(COD) (6.2 mg, 0.015 mmol, 1.5 mol % Ir), and dmpe (3.0 mg, 0.02 mmol, 2 mol %) were weighed in test tubes. Excess HBPin (typically, 1.5 to 2 equivalents of boron) was used to dissolve and mix the (Ind)Ir(COD) and dmpe, and the resulting solution was transferred to the Schlenk flask. The flask was sealed, removed from the glove box, and stirred at 150 oC. until the reaction was judged complete by GC-FID. The Schlenk flask was taken back into the glove box and the crude material was washed with pentane to remove excess HBPin.

Crystallization from pentane at −80 oC. afforded the desired product.

EXAMPLES

Preparation of 1-methyl-5-(4,4,5,5-tetramethyl-1,3,2-dioxaborolan-2-yl)-1H-imidazole

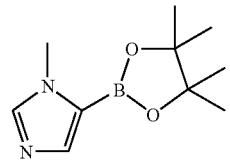

General procedure A was applied to 1-methylimidazole (82.1 mg, 79 μL, 1 mmol, 1 equiv) and HBPin (218 μL, 192 mg, 1.5 mmol, 1.5 equiv) at room temperature. The crude reaction mixture was washed with pentane (3.0 mL portions until the pentane wash is completely colorless) inside the glovebox. The washed product was dried to afford 1-methyl-5-(4,4,5,5-tetramethyl-1,3,2-dioxaborolan-2-yl)-1H-imidazole (152 mg, 73%) as a white solid. 1H, 13C NMR, gHMQC and gHMBC spectroscopy were used to assign the diborylated product as 1-methyl-5-(4,4,5,5-tetramethyl-1,3,2-dioxaborolan-2-yl)-1H-imidazole. 1H NMR (CDC13, 500 MHz): δ 7.55 (d, J=0.7 Hz, 1H), 7.54 (br s, 1H), 3.77 (s, 1H), 1.30 (s, 12H, CH3 of pinacolate); 13C NMR {1H} (CDC13, 125 MHz): δ 141.7, 141.4, 83.6, 33.9, 24.8; 11B NMR (CDC13, 96 MHz): δ 28.5; FT-IR (neat): 3160, 2958, 2926, 2855, 1553, 1460, 1377, 1177, 1155, 1030, 1005, 804, 779, 740, 640 cm-1; LRMS (% rel. int.): m/e 209 (23), 208 M (94), 207 M+ (100), 206(19), 193(33), 165(57), 123(16), 109(39), 108(48).

Preparation of 1,2-dimethyl-5-(4,4,5,5-tetramethyl-1,3,2-dioxaborolan-2-yl)-1H-imidazole

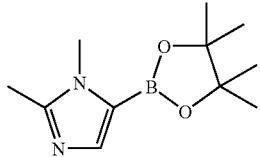

General procedure A was applied to 1,2-dimethylimidazole (96.1 mg, 1 mmol, 1 equiv) and HBPin (218 μL, 192.0 mg, 1.5 mmol, 1.5 equiv) in pentane/ether (1:2 v/v) for 9 h. The crude reaction mixture was washed with pentane (3.0 mL portions until the pentane wash is completely colorless) inside the glovebox. The washed product was dried to afford the desired product 1,2-dimethyl-5-(4,4,5,5-tetramethyl-1,3,2-dioxaborolan-2-yl)-1H-imidazole (196 mg, 88%, 209 mg, 94%) as a white solid. 1H and 13C NMR spectroscopy, gHMQC were used to assign the borylated product as 5 (4,4,5,5-tetramethyl-1,3,2-dioxaboryl)-1,2 dimethylimidazole. 1H NMR (CDCl3, 300 MHz): δ 7.41 (s, 1H, Ha), 3.65 (s, 3H, CH3), 2.34 (s, 3H, CH3), 1.27 (s, 12H, CH3 of pinacolate); 13C NMR {1H} (CDCl3, 75 MHz): δ 149.3, 140.2, 83.3, 32.6, 24.8, 13.2. 11B NMR (CDCl3, 96 MHz): δ 28.4. FT-IR (mineral oil): 29255, 2926, 2855, 1458, 1377, 1169, 1026, 721 cm-1; LRMS (% rel. int.): m/e; 223(16), 222 M (100), 221 M+ (74), 207(29), 179(35), 137(19), 123(30), 122(43), 121(20).

Preparation of 2-bromo-1-methyl-5-(4,4,5,5-tetramethyl-1,3,2-dioxaborolan-2-yl)-1H-imidazole

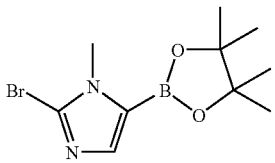

General procedure A was applied to 1-methylimidazole (161.1 mg, 1 mmol, 1 equiv) and HBPin (218 μL, 192 mg, 1.5 mmol, 1.5 equiv) at room temperature for 61/2 h. The crude reaction mixture was washed with pentane (3.0 mL portions until the pentane wash is completely colorless) inside the glovebox. The washed product was dried to afford 2-bromo-1-methyl-5-(4,4,5,5-tetramethyl-1,3,2-dioxaborolan-2-yl)-1H-imidazole (226 mg, 79%) as a white solid, m.p. 124-127° C. 1H, 13C NMR, gHMQC and gHMBC spectroscopy were used to assign the diborylated product as 1-methyl-5-(4,4,5,5-tetramethyl-1,3,2-dioxaborolan-2-yl)-1H-imidazole.

1H NMR (CDCl3, 500 MHz): δ 7.47 (s, 1H), 3.73 (s, CH3), 1.28 (s, 12H, CH3 of pinacolate); 13C NMR {1H} (CDCl3, 125 MHz): δ 141.7, 125.3, 83.9, 34.6, 24.7; 11B NMR (CDCl3, 96 MHz): δ 27.8; FT-IR (mineral oil): 2955, 2924, 2855, 1543, 1462, 1401, 1377, 1319, 1230, 1144, 1804, 964, 935, 854, 721 cm-1; LRMS (% rel. int.): m/e 288 M+1 (87), 287 M+ (100), 286 M+ (100), 285(84), 273(23), 271 (23), 188(31), 187(22), 186(26); Anal. Calcd for C10H16BBrN2O2: C, 41.85; H, 5.62; N, 9.76. Found: C, 41.93; H, 5.62; N, 9.71.

Preparation of 1-methyl-2-phenyl-5-(4,4,5,5-tetramethyl-1,3,2-dioxaborolan-2-yl)-1H-imidazole

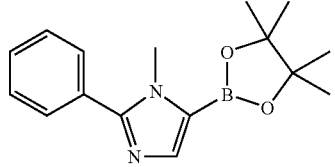

General procedure A was applied to 1-methyl-2-phenylimidazole (158.2 mg, 1 mmol, 1 equivalent) and HBPin (218 μL, 192.0 mg, 1.5 mmol, 1.5 equivalents) in ether for 6 h. The crude reaction mixture was washed with pentane (3.0 mL portions until the pentane wash is completely colorless) inside the glovebox. The washed product was dried to afford 1-methyl-2-phenyl-5-(4,4,5,5-tetramethyl-1,3,2-dioxaborolan-2-yl)-1H-imidazole (180.0 mg, 63%) as a white solid. 1H, 13C NMR, gHMQC and gHMBC spectroscopy were used to assign the diborylated product as 1-methyl-2-phenyl-5-(4,4,5,5-tetramethyl-1,3,2-dioxaborolan-2-yl)-1H-imidazole.

1-methyl-2-phenyl-5-(4,4,5,5-tetramethyl-1,3,2-dioxaborolan-2-yl)-1H-imidazole::1H NMR (CDCl3, 500 MHz): δ 7.65 (s, 1H), 7.61 (dd, J=2.1, 1.6 Hz 2H), 7.60 (dd, J=1.9, 1.6 Hz, 3H), 7.45-7.40 (m, 3H), 3.84 (s, 3H, NCH3), 1.32 (s, 12H, CH3 of pinacolate); 13C NMR {1H} (CDCl3, 125 MHz): δ 152.2, 141.5, 130.7, 129.1, 128.8, 128.4, 83.6, 34.4, 24.8; 11B NMR (CDCl3, 96 MHz): δ 28.6; FT-IR (mineral oil): 3455, 2980, 1483, 1373, 1326, 1282, 1217, 1126, 1041, 852, 752 cm-1; LRMS (% rel. int.): m/e 285(19), 284(100) M+ (100), 283(88), 183(15); Anal. Calcd for C16H21BN2O2: C, 67.63; H, 7.45; N, 9.86. Found: C, 67.10; H, 7.54; N, 9.88.

Preparation of 1-methyl-5-(4,4,5,5-tetramethyl-1,3,2-dioxaborolan-2-yl)-2-(2-(4,4,5,5-tetramethyl-1,3,2-dioxaborolan-2-yl)phenyl)-1H-imidazole

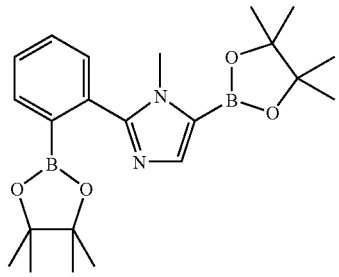

General procedure A was applied to 1-methyl-2-phenylimidazole (158.2 mg, 1 mmol, 1 equivalent) and HBPin (363 μL, 320.0 mg, 2.5 mmol, 2.5 equivalents) in ether. The crude reaction mixture was washed with pentane (3.0 mL portions until the pentane wash is completely colorless) inside the glovebox. The washed product was dried to afford 1-methyl-5-(4,4,5,5-tetramethyl-1,3,2-dioxaborolan-2-yl)-2-(2-(4,4,5,5-tetramethyl-1,3,2-dioxaborolan-2-yl)phenyl)-1H-imidazole (322.0 mg, 78%) as a white solid. 1H, 13C NMR, gHMQC and gHMBC spectroscopy were used to assign the diborylated product as 1-methyl-5-(4,4,5,5-tetramethyl-1,3,2-dioxaborolan-2-yl)-2-(2-(4,4,5,5-tetramethyl-1,3,2-dioxaborolan-2-yl)phenyl)-1H-imidazole 1H NMR (CDCl3, 500 MHz): δ 7.69-7.67 (dt, J=7.1, 1.0 Hz, 1H), 7.57 (s, 1H), 7.48-7.46 (dt, J=7.5, 0.8 Hz, 1H), 7.35-7.32 (td, J=7.3, 1.0 Hz, 1H), 7.26-7.23 (td, J=7.5, 1.2 Hz, 1H), 3.97 (s, 3H, CH3), 1.32 (s, 12H, CH3 of pinacolate), 1.31 (s, 12H, CH3 of pinacolate); 13C NMR {1H} (CDCl3, 125 MHz): δ 154.3, 134.1, 132.1, 131.1, 130.1, 127.5, 121.4, 84.2, 80.2, 34.1, 25.7, 24.7; 11B NMR (CDCl3, 96 MHz): δ 28.0, 13.1; FT-IR (mineral oil): 3422(v. br), 2924, 2855, 1560, 1458, 1417(w), 1377, 1310, 1261, 1236(w), 1146, 1115, 1092, 1066, 1028, 964, 854, 721, 683 cm-1; LRMS (% rel. int.): m/e 410 (35), 409 M+ (100), 408(51), 352(26), 351(37), 236(15), 327(29), 284(16); Anal. Calcd for C22H32B2N2O4: C, 64.43; H, 7.86; N, 6.83. Found: C, 63.70; H, 8.04; N, 6.67.

Preparation of 1-benzyl-5-(4,4,5,5-tetramethyl-1,3,2-dioxaborolan-2-yl)-1H-imidazole General procedure A was applied to 1-methyl-2-phenylimidazole (158.2 mg, 1 mmol, 1 equivalent) and HBPin (218 μL, 192.0 mg, 1.5 mmol, 1.5 equivalents) in ether for (overnight). The crude reaction mixture was washed with pentane (3.0 mL portions until the pentane wash is completely colorless) inside the glovebox. The washed product was dried to afford 1-benzyl-5-(4,4,5,5-tetramethyl-1,3,2-dioxaborolan-2-yl)-1H-imidazole (236 mg, 83%) as a white solid, mp 161.5-162.5° C. 1H, 13C NMR, gHMQC and gHMBC spectroscopy were used to assign the diborylated product as 1-benzyl-5-(4,4,5,5-tetramethyl-1,3,2-dioxaborolan-2-yl)-1H-imidazole 1H NMR (CDCl3, 500 MHz): δ 7.62 (d, J=0.8 Hz, 1H), 7.60 (d, J=0.8 Hz, 1H), 7.29-7.21 (m, 3H), 7.11-7.09 (d, J=6.1 Hz, 2H), 5.33 (s, 2H), 1.21 (s, 12H, CH3 of pinacolate); 13C NMR {1H} (CDCl3, 125 MHz): δ 142.3, 141.7, 137.6, 128.5, 127.6, 127.1, 83.7, 50.4, 24.6; 11B NMR (CDCl3, 96 MHz): δ 28.9; FT-IR (neat): 3154, 2924, 2855, 1456, 1377, 1155, 1091, 1024, 1001, 847, 781, 760, 725, 684, 640 cm-1; LRMS (% rel. int.): m/e 285(24), 284 M+ (100), 283(48), 185(21), 184(90), 183(35), 91(58); Anal. Calcd for C16H21BN2O2: C, 67.63; H, 7.45; N, 9.86. Found: C, 67.43; H, 6.99; N, 9.74.

Preparation of N-methyl-N-(5-(4,4,5,5-tetramethyl-1,3,2-dioxaborolan-2-yl)-1H-imidazol-1-ylthioperoxy)-methanamine

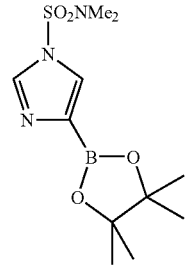

General procedure A was applied to N,N-dimethyl imidazole-1-sulfonamide (175 mg, 1.0 mmol, 1.0 equiv) and B2Bpin2 (254 mg, 1.0 mmol (2.0 mmol B), 1.0 equiv) in ether at room temperature for 65 h. The crude reaction mixture was washed with pentane (3.0 mL portions until the pentane wash is completely colorless) inside the glovebox. The washed product was dried to afford N-methyl-N-(5-(4,4,5,5-tetramethyl-1,3,2-dioxaborolan-2-yl)-1H-imidazol-1-ylthioperoxy)-methanamine (249 mg, 82%) as an off-white solid, 118-122° C. (sublim). 1H, 13C NMR, gHMQC and gHMBC spectroscopy were used to assign the diborylated product as N-methyl-N-(5-(4,4,5,5-tetramethyl-1,3,2-dioxaborolan-2-yl)-1H-imidazol-1-ylthioperoxy)-methanamine 1H NMR (CDCl3, 500 MHz): δ 7.97 (s, 1H, Ha), 7.66 (s, 1H, Hb), 2.83 (s, 6H, N(CH3)2), 1.32 (br s, 12H, CH3 of pinacolate); 13C NMR {1H} (CDCl3, 75 MHz): δ 137.9, 127.0, 84.2, 38.2, 24.8; 11B NMR (CDCl3, 96 MHz): δ 29.0; m/e 301 (68), 300 M+ (24), 286(28), 202(20), 193 (100), 192(28), 149(22), 135 (52), 109(30), 108(42)95(19), 43(25); Anal. Calcd for C11H20BN3O4S: C, 43.87; H, 6.69; N, 13.95. Found: C, 43.32; H, 6.23; N, 13.73.

Preparation of 3-(4,4,5,5-tetramethyl-1,3,2-dioxaborolan-2-yl)H-imidazo[1,2-a]pyridine

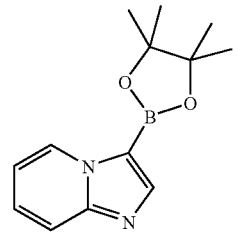

General procedure A was applied to imidazo[1,2-a]pyridine (118.0 mg, 101 μL, 1.0 mmol, 1.0 equiv) and HBPin (218 μL, 192 mg, 1.5 mmol, 1.5 equiv) at room temperature for 1.5 h. The crude reaction mixture was washed with pentane (3.0 mL portions until the pentane wash is completely colorless) inside the glovebox. The washed product was dried to afford 3-(4,4,5,5-tetramethyl-1,3,2-dioxaborolan-2-yl)H-imidazo [1,2-a]pyridine (233 mg, 91%) as an off-white solid. 1H, 13C NMR, gHMQC and gHMBC spectroscopy were used to assign the diborylated product as 3-(4,4,5,5-tetramethyl-1,3, 2-dioxaborolan-2-yl)H-imidazo[1,2-a]pyridine 1H NMR (CDCl3, 500 MHz): δ 8.80-8.74 (dt, J=6.8, 1.2 Hz, 1H, Ha), 7.64-7.61 (dt, J=9.0, 1.0 Hz, 1H), 7.24-7.20 (d?, J=6.8, 6.6, 1.9, 1.2 Hz, 1H), 6.84-6.80 (td, J=6.8, 6.6, 1.2, 1.0 Hz 1H, Hb), 1.34 (br s, 12H, CH3 of pinacolate); 13C NMR {1H} (CDCl3, 125.7 MHz): δ 148.9, 145.5, 128.8, 125.8, 117.4, 112.6, 83.8, 24.8; 11B NMR (CDCl3, 96 MHz): δ 28.5; FT-IR (neat): 2957, 2924, 2855, 1641, 1512, 1460, 1379, 1360, 1286, 1174, 1138, 1091, 1016, 970, 794, 775, 758, 679, 640 cm-1; LRMS [EI] (% rel. int.): m/e 244 M (100), 243(36), 229(27), 145(20), 144(36), 78(25); Anal. Calcd for C13H17BN2O2: C, 63.97; H, 7.02; N, 11.48.

Preparation of 1-methyl-5-(4,4,5,5-tetramethyl-1,3,2-dioxaborolan-2-yl)-1H-pyrazole and 1-methyl-4-(4,4,5,5-tetramethyl-1,3,2-dioxaborolan-2-yl)-1H-pyrazole

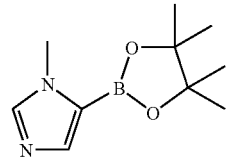

General procedure A was applied to 1-methylpyrazole (82.1 mg, 1.0 mmol, 1.0 equiv) and HBPin (218 μL, 192 mg, 1.5 mmol, 1.5 equiv) in pentane/thf (2:1 v/v) at room temperature for 5 h. The products were isolated by passing a solution of the crude reaction mixture in CH2Cl₂ through a plug of silica gel (buffered with >10% TEA) and eluting with CH2Cl₂ to afford a 91:9 mixture of 1-methyl-5-(4,4,5,5-tetramethyl-1,3,2-dioxaborolan-2-yl)-1H-pyrazole and 1-methyl-4-(4,4,5,5-tetramethyl-1,3,2-dioxaborolan-2-yl)-1H-pyrazole (155 mg, 74%) as a white solid. 1H, 13C NMR, gHMQC and gHMBC spectroscopy were used to assign the monoborylated products as 1-methyl-5-(4,4,5,5-tetramethyl-1,3,2-dioxaborolan-2-yl)-1H-pyrazole and 1-methyl-4-(4,4,5,5-tetramethyl-1,3,2-dioxaborolan-2-yl)-1H-pyrazole respectively.

1-methyl-5-(4,4,5,5-tetramethyl-1,3,2-dioxaborolan-2-yl)-1H-pyrazole Major isomer: 1H NMR (CDC13, 500 MHz): δ 7.46 (d, J=1.9 Hz, 1H), 6.69 (d, J=1.9 Hz, 1H), 4.06 (s, 3H), 1.32 (s, 12H, CH3 of pinacolate); 13C NMR {1H} (CDC13, 75 MHz): δ 138.3, 115.7, 84.1, 39.3, 24.8; 11B NMR (CDC13, 96 MHz): δ 28.1; FT-IR (mineral oil): 2928, 2855, 1533, 1458, 1377, 1350, 1251, 1145, 1101, 1009, 856, 794, 721, 700 cm-1; LRMS (% rel. int.): m/e 210(12), 209 M+ (100), 208(29); Anal. Calcd for C10H17BN2O2: C, 57.73; H, 8.24; N, 13.46. Found: C, 57.82; H, 8.38; N, 14.05.

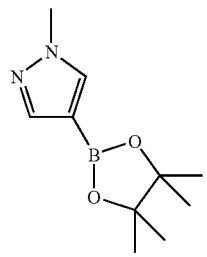

1-methyl-4-(4,4,5,5-tetramethyl-1,3,2-dioxaborolan-2-yl)-1H-pyrazole (minor isomer): LRMS (% rel. int.): m/e 210(12), 209 M+ (92), 208(44), 193(100), 192(27), 122(19), 109(82), 108(29).

Prepaqration of 4-bromo-1-methyl-5-(4,4,5,5-tetramethyl-1,3,2-dioxaborolan-2-yl)-1H-pyrazole and 4-bromo-1-methyl-3,5-bis(4,4,5,5-tetramethyl-1,3,2-dioxaborolan-2-yl)-1H-pyrazole

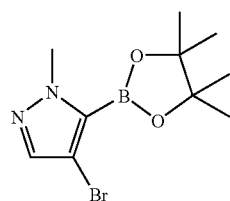

General procedure A was applied to 4-bromo-1-methylpyrazole (161.0 mg, 1.0 mmol, 1.0 equiv) and HBPin (218 µL, 192 mg, 1.5 mmol, 1.5 equiv) at room temperature for 5 h. The crude reaction mixture was washed with pentane (3.0 mL portions until the pentane wash is completely colorless) inside the glovebox. The washed product was dried to afford a 88:12 mixture of 4-bromo-1-methyl-5-(4,4,5,5-tetramethyl-1,3,2-dioxaborolan-2-yl)-1H-pyrazole (m.p. 72-74° C.) and 4-bromo-1-methyl-3,5-bis(4,4,5,5-tetramethyl-1,3,2-dioxaborolan-2-yl)-1H-pyrazole (m.p. 220-221° C.) (195 mg, 68%) as an off-white solid, mp 72-74° C. 1H, 13C NMR, gHMQC and gHMBC spectroscopy were used to assign the mono- and diborylated products as 4-bromo-1-methyl-5-(4,4,5,5-tetramethyl-1,3,2-dioxaborolan-2-yl)-1H-pyrazole and 4-bromo-1-methyl-3,5-bis(4,4,5,5-tetramethyl-1,3,2-dioxaborolan-2-yl)-1H-pyrazole respectively 1H NMR (CDC13, 300 MHz): δ 7.43 (s, 1H), 4.03 (s, 3H, CH3), 1.33 (br s, 12H, CH3 of pinacolate); 11B NMR (CDC13, 96 MHz): δ 27.7. LRMS (% rel. int.): m/e 289(29), 288(99), 287(56), 286 M+ (100), 285(26), 208(11), 207(81), 206(21), 165(100), 164(31); Anal. Calcd for C10H16BBrN2O2: C, 41.85; H, 5.62; N, 9.76. Found: C, 41.66; H, 5.57; N, 9.71.

Preparation of 4-bromo-1-methyl-3,5-bis(4,4,5,5-tetramethyl-1,3,2-dioxaborolan-2-yl)-1H-pyrazole

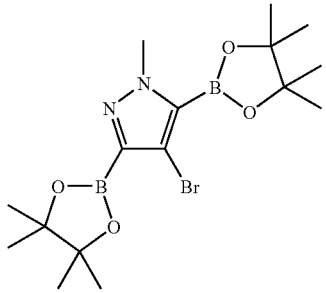

General procedure A was applied to 4-bromo-1-methylpyrazole (161.0 mg, 1.0 mmol, 1.0 equiv) and HBPin (435 µL, 384 mg, 3.0 mmol, 3.0 equiv) at room temperature for 36 h. The crude reaction mixture was washed with pentane (3.0 mL portions until the pentane wash is completely colorless) inside the glovebox. The washed product was dried to afford 4-bromo-1-methyl-3,5-bis(4,4,5,5-tetramethyl-1,3,2-dioxaborolan-2-yl)-1H-pyrazole (80 mg) as an off-white solid, mp 72-74° C. 1H, 13C NMR, gHMQC and gHMBC spectroscopy were used to assign the diborylated product as 4-bromo-1-methyl-3,5-bis(4,4,5,5-tetramethyl-1,3,2-dioxaborolan-2-yl)-1H-pyrazole m.p. 220-221° C. 1H NMR (CDC13, 500 MHz): δ 4.08 (s 3H, CH3), 1.33 (s, 12H, CH3 of pinacolate), 1.32 (s, 12H, CH3 of pinacolate); 11B NMR (CDC13, 96 MHz): δ 28.07; LRMS (% rel. int.): m/e 415(96), 414(69), 413 M (100), 412 M+ (55); Anal. Calcd for C16H27B2BrN2O2: C, 46.54; H, 6.59; N, 6.78. Found: C, 46.78; H, 6.51; N, 6.71.

Preparation of 5-(4,4,5,5-Tetramethyl-[1,3,2]dioxaborolan-2-yl)-oxazole

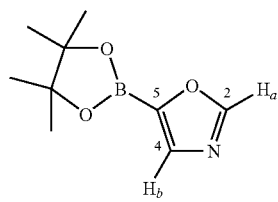

The general borylation procedure A was applied to oxazole (66 µL, 69 mg, 1.00 mmol, 1 equiv) and HBPin (160 µL, 141 mg, 1.10 mmol, 1.10 equiv) at room temperature for 5 min. The product was isolated as a pale yellow solid. (117 mg, 60% yield). 1H NMR (CDC13, 300 MHz): δ 8.02 (s, 1H, Ha), 7.61

(s, 1H, Hb), 1.30 (br s, 12H, CH3 of BPin); 13C NMR {1H} (CDC13, 75 MHz): δ 154.7 (CH), 138.8 (CH), 84.7 (C), 24.6 (4 CH3 of BPin); 11B NMR (CDC13, 96 MHz): δ 27.4; GC-MS (EI) m/z (% relative intensity): (M+1)+196 (100), 180 (7), 153 (16), 109 (37).

The compounds below were similarly prepared from their parent hydrocarbon compounds where H is substituted in place of BPin

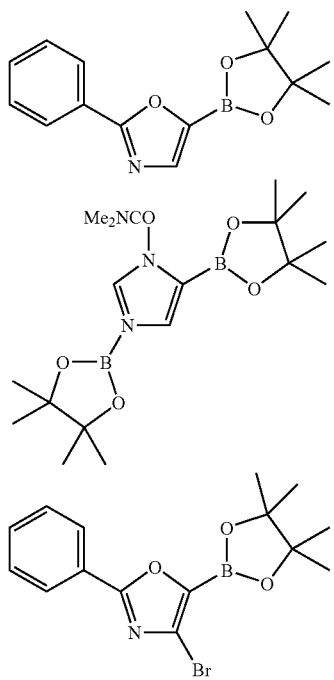

REFERENCES

[a] *The Chemistry of Heterocyclic Compounds, Volume 60, Oxazoles: Synthesis, Reactions, and Spectroscopy, Part A*; Palmer, D. C., Ed.; Wiley & Sons: New York, 2003.

[b] Romero, F. A.; Du, W.; Hwang, I.; Rayl, T. J.; Kimball, F. S.; Leung, D.; Hoover, H. S.; Apodaca, R. L.; Breitenbucher, J. G.; Cravatt, B. F.; Boger, D. L. *J. Med. Chem.* 2007, 50, 1058-1068.

[c] Hashimoto, H.; Imamura, K.; Haruta, J.; Wakitani, K. *J. Med. Chem.* 2002, 45, 1511-1517.

[d] Harris, P. A.; Cheung, M.; Hunter, R. N., III; Brown, M. L.; Veal, J. M.; Nolte, R. T.; Wang, L.; Liu, W.; Crosby, R. M.; Johnson, J. H.; Epperly, A. H.; Kumar, R.; Luttrell, D. K.; Stafford, J. A. *J. Med. Chem.* 2005, 48, 1610-1619.

[e] Brown, P.; Davies, D. T.; O'Hanlon, P. J.; Wilson, J. M. *J. Med. Chem.* 1996, 39, 446-457.

[f] Razavi, H.; Powers, E. T.; Purkey, H. E.; Adamski-Werner, S. L.; Chiang, K. P.; Dendle, M. T. A.; Kelly, Jeffery W. *Bioorg. Med. Chem. Lett.* 2005, 15, 1075-1078.

The compounds of the present invention are intermediates to natural cytotoxic compounds which have cytotoxic, anticancer and antiviral activity. The compounds are also intermediates to synthetic anticancer and antiviral agents based upon the N-protected compounds as intermediates.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

The invention claimed is:

1. A process for producing an oxazole (I), imidazole (II), or pyrazole (III) boryl compound, the process comprising:

(a) reacting an oxazole (IV), imidazole (V), or pyrazole (VI) with an HB or B—B organic compound in a reaction mixture with a non-reactive solvent at a temperature between about 0° C. and 150° C. and in the presence of a catalytically effective amount of an iridium complex catalytic composition, the oxazole (IV), imidazole (V), or pyrazole (VI) having a structure according to formula IV, V, or VI, respectively:

IV

V

VI wherein:

(i) $R_1$ is independently selected from the group consisting of hydrogen, boryl, halo, cyano, alkyl, alkoxy, thioalkyl, amino alkyl, acyl, alkyl aminoacyl, trifluoro alkyl, aryl, alkyl silyl, and containing 1 to 8 carbon atoms except for the halo group and boryl group, (ii) $R_2$ is selected from the group consisting of methyl, isopropyl, triisopropylsilyl, phenyl, benzyl, para-methoxybenzyl, tert-butoxycarbonyl, (benzyloxy)carbonyl, N,N-dimethylaminosulfonyl, N,N-dimethylcarboxamide, para-toluenesulfonyl, and 9H-Fluoren-9-ylmethyloxycarbonyl; and (iii) the iridium complex catalytic composition comprises an iridium complex of the formula: $(BY)_n$-Ir-(ligand)$_m$, where n is equal to one to five, m is equal to one to three, excluding hydrogen, bonded to the iridium, BY is a boron moiety, the ligand is selected from the group consisting of a phosphorus organic ligand, an organic amine, an imine, a nitrogen heterocycle, and an ether, and the ligand is at least in part bonded to the iridium;

(b) forming the oxazole (I), imidazole (II), or pyrazole (III) boryl compound in the reaction mixture, the oxazole (I), imidazole (II), or pyrazole (III) boryl compound having a structure according to formula I, II, or III, respectively:

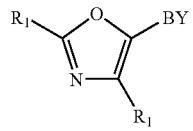

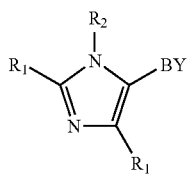

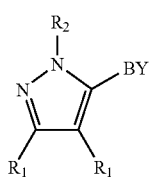

wherein:
(i) $R_1$ is independently selected from the group consisting of hydrogen, boryl, halo, cyano, alkyl, alkoxy, thioalkyl, amino alkyl, acyl, alkyl aminoacyl, trifluoro alkyl, aryl, alkyl silyl, and containing 1 to 8 carbon atoms except for the halo group and boryl group,
(ii) $R_2$ is selected from the group consisting of methyl, isopropyl, triisopropylsilyl, phenyl, benzyl, para-methoxybenzyl, tert-butoxycarbonyl, (benzyloxy)carbonyl, N,N-dimethylaminosulfonyl, N,N-dimethylcarboxamide, para-toluenesulfonyl, and 9H-Fluoren-9-ylmethyloxycarbonyl; and
(c) evaporating the solvent and portions of the reaction mixture which are volatile from the reaction mixture to produce the oxazole (I), imidazole (II), or pyrazole (III) boryl compound.

2. The process of claim 1 wherein the iridium complex catalytic composition is formed in the reaction mixture from an iridium complex of $[Ir(OMe)(COD)]_2$, $[Ir(Cl)(COD)]_2$, or $(COD)(\eta^5\text{-indenyl})Ir$, where COD is 1,5-cyclooctadine, complexed with a ligand selected from the group consisting of:

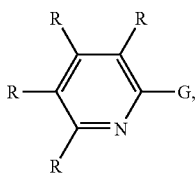 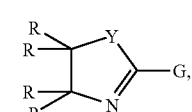

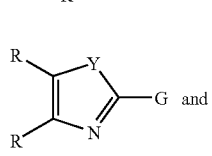 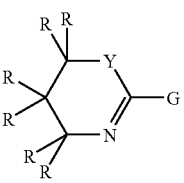

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and G is a heteroatom containing group, multiple atom chain, or multiple atom ring.

3. The process of claim 1 wherein the iridium complex catalytic composition is formed in the reaction mixture from an iridium complex of $[Ir(OMe)(COD)]_2$, $[Ir(Cl)(COD)]_2$, or $(COD)(\eta^5\text{-indenyl})Ir$, where COD is 1,5-cyclooctadine, complexed with a ligand selected from the group consisting of:

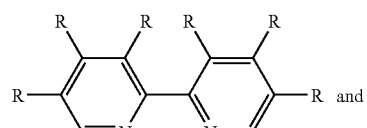

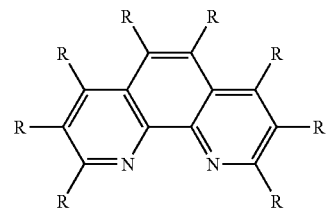

wherein R are each selected from the group consisting of hydrogen, linear alkyl containing 1 to 8 carbon atoms, branched alkyl containing 1 to 8 carbons, and a carbon in a cyclic structure.

4. The process of claim 1 wherein the iridium complex catalytic composition is formed in the reaction mixture from an iridium complex of $[Ir(OMe)(COD)]_2$, $[Ir(Cl)(COD)]_2$, or $(COD)(\eta^5\text{-indenyl})Ir$, where COD is 1,5-cyclooctadine, complexed with a ligand selected from the group consisting of:

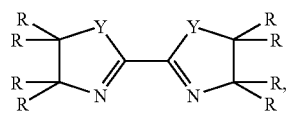

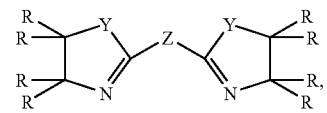

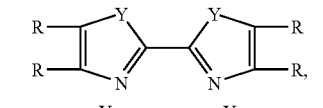

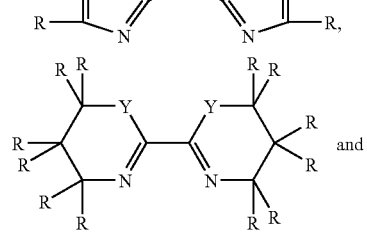

-continued

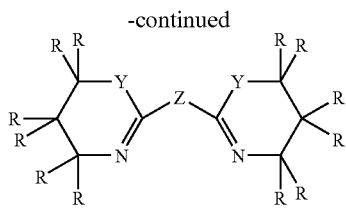

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and Z is a carbon, oxygen, nitrogen, sulfur, or boron containing moiety or a multiple atom chain containing a carbon, oxygen, nitrogen, sulfur, or boron containing moiety.

5. The process of claim 1 wherein the iridium complex catalytic composition is formed in the reaction mixture from an iridium complex of $[Ir(OMe)(COD)]_2$, $[Ir(Cl)(COD)]_2$, or $(COD)(\eta^5\text{-indenyl})Ir$, where COD is 1,5-cyclooctadiene, complexed with a ligand selected from the group consisting of:

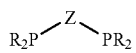

wherein R are each selected from the group consisting of hydrogen, aryl, linear alkyl containing 1 to 8 carbon atoms, branched alkyl containing 1 to 8 carbons, alkoxy, or a carbon in a cyclic structure and Z is a carbon, oxygen, or nitrogen containing moiety or a multiple atom chain containing a carbon, oxygen, or nitrogen containing moiety.

6. The process of claim 1 wherein the iridium complex catalytic composition is formed in the reaction mixture from an iridium complex of $[Ir(OMe)(COD)]_2$, $[Ir(Cl)(COD)]_2$, or $(COD)(\eta^5\text{-indenyl})Ir$, where COD is 1,5-cyclooctadiene, complexed with 4,4-di-t-butyl-2,2'-bipyridine (dtbpy).

7. The process of claim 1 wherein the iridium complex catalytic composition is formed in the reaction mixture from an iridium complex of $[Ir(OMe)(COD)]_2$, $[Ir(Cl)(COD)]_2$, or $(COD)(\eta^5\text{-indenyl})Ir$, where COD is 1,5-cyclooctadiene, complexed with 1,2-bis(dimethylphospino)ethane.

8. The process of claim 1 wherein the non-reactive solvent is selected from the group consisting of aliphatic hydrocarbons, ethers, and combinations thereof.

9. The process of claim 1 wherein:
(i) the reaction mixture comprises the oxazole (IV) prior to reaction; and
(ii) the boryl compound formed in the reaction mixture comprises the oxazole (I) boryl compound.

10. The process of claim 1 wherein:
(i) the reaction mixture comprises the imidazole (V) prior to reaction; and
(ii) the boryl compound formed in the reaction mixture comprises the imidazole (II) boryl compound.

11. The process of claim 1 wherein:
(i) the reaction mixture comprises the pyrazole (VI) prior to reaction;
(ii) the boryl compound formed in the reaction mixture comprises the pyrazole (III) boryl compound;

(iii) $R_1$ at the 3-position and $R_1$ at the 4-position of the pyrazole (VI) and the pyrazole (III) boryl compound together are not hydrogen and hydrogen, respectively; and
(iv) $R_1$ at the 3-position and $R_1$ at the 4-position of the pyrazole (VI) and the pyrazole (III) boryl compound together are not alkyl and hydrogen, respectively.

12. An oxazole (I), imidazole (II), or pyrazole (III) boryl compound having a structure according to formula I, II, or III, respectively:

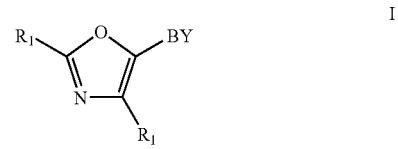

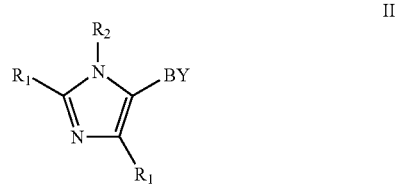

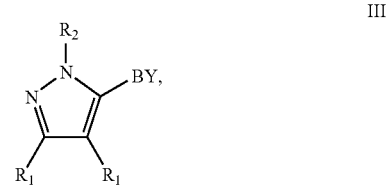

wherein:
(i) $R_1$ is independently selected from the group consisting of hydrogen, boryl, halo, cyano, alkyl, alkoxy, thioalkyl, amino alkyl, acyl, alkyl aminoacyl, trifluoro alkyl, aryl, alkyl silyl, and containing 1 to 8 carbon atoms except for the halo group and boryl group,
(ii) $R_2$ is selected from the group consisting of methyl, isopropyl, triisopropylsilyl, phenyl, benzyl, para-methoxybenzyl, tert-butoxycarbonyl, (benzyloxy)carbonyl, N,N-dimethylaminosulfonyl, N,N-dimethylcarboxamide, para-toluenesulfonyl, and 9H-Fluoren-9-ylmethyloxycarbonyl, and
(iii) BY is a boron moiety derived from an HB or B—B organic compound;
(iv) $R_1$ at the 2-position and $R_1$ at the 4-position of the oxazole (I) boryl compound together are not hydrogen and hydrogen, respectively;
(v) $R_1$ at the 2-position and $R_1$ at the 4-position of the imidazole (II) boryl compound together are not alkyl and hydrogen, respectively;
(vi) $R_1$ at the 3-position and $R_1$ at the 4-position of the pyrazole (III) boryl compound together are not hydrogen and hydrogen, respectively; and
(vii) $R_1$ at the 3-position and $R_1$ at the 4-position of the pyrazole (III) boryl compound together are not alkyl and hydrogen, respectively.

13. The compound of claim 12 wherein at least one $R_1$ substituent is a halo group.

14. The compound of claim 12 wherein at least one $R_1$ substituent is an aryl group.

15. The compound of claim 12 comprising the oxazole (I) boryl compound.

16. The compound of claim 12, comprising an oxazole (I) boryl compound selected from the group consisting of:

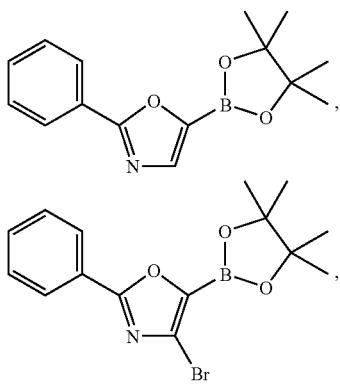

and combinations thereof.

17. The compound of claim 12, comprising the imidazole (II) boryl compound.

18. The compound of claim 12, comprising an imidazole (II) boryl compound selected from the group consisting of:

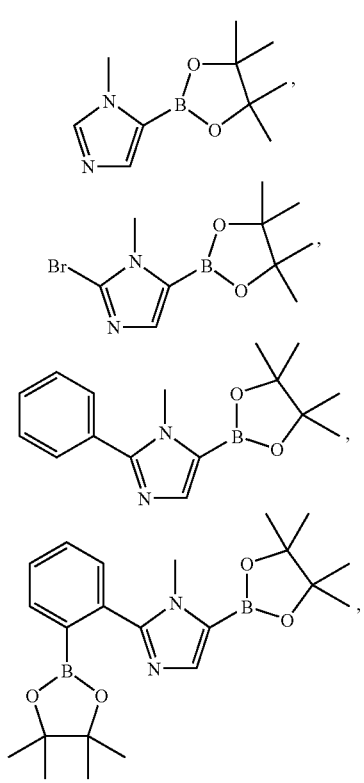

-continued

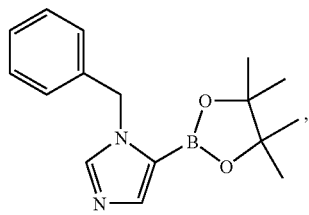

and combinations thereof.

19. The compound of claim 12, comprising the pyrazole (III) boryl compound.

20. The compound of claim 12, comprising a pyrazole (III) boryl compound selected from the group consisting of:

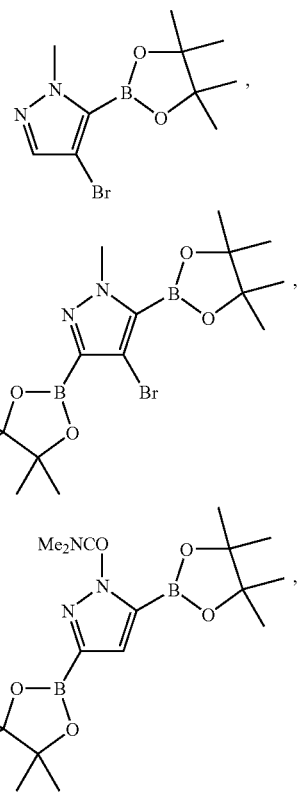

and combinations thereof.

* * * * *

UNITED STATES PATENT AND TRADEMARK OFFICE
CERTIFICATE OF CORRECTION

PATENT NO. : 7,709,654 B2
APPLICATION NO. : 11/900329
DATED : May 4, 2010
INVENTOR(S) : Milton R. Smith, III et al.

It is certified that error appears in the above-identified patent and that said Letters Patent is hereby corrected as shown below:

Column 5, line 65, "[Ir(OMe)(COD)]2" should be -- [Ir(OMe)(COD)]$_2$ --.

Column 6, line 25, "150 oC" should be -- 150°C --.

Column 6, line 30, "-80 oC" should be -- -80°C --.

Column 10, line 10, "108(42)$_{95}$(19)" should be -- 108(42)95(19) --.

Column 10, lines 55-65, " 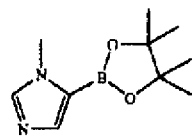 " should be -- 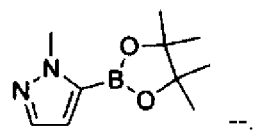 --.

Column 11, line 2, "CH2Cl$_2$" should be -- CH2Cl2 --.

Column 11, line 4, "CH2Cl$_2$" should be -- CH2Cl2 --.

Column 13, lines 15-25, " 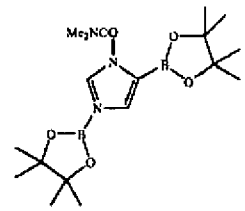 " should be -- 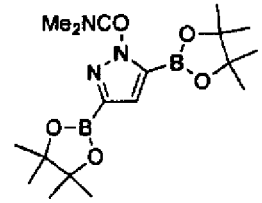 --.

Column 14, line 11, Claim 1, "HB or B-B organic compound" should be -- HBPin or B$_2$Pin$_2$ --.

Column 14, line 58, Claim 1, "BY is a boron moiety" should be -- BY is Bpin --.

Signed and Sealed this

Tenth Day of August, 2010

David J. Kappos
*Director of the United States Patent and Trademark Office*

CERTIFICATE OF CORRECTION (continued)
U.S. Pat. No. 7,709,654 B2

Column 18, line 47, Claim 12, "BY is a boron moiety derived from an HB or B-B organic compound" should be -- BY is BPin --.

Column 18, line 66, Claim 15, "comprising" should be -- consisting of --.

Column 19, line 1, Claim 16, "comprising" should be -- having --.

Column 19, line 4, Claim 17, "comprising" should be -- consisting of --.

Column 19, line 6, Claim 18, "comprising" should be -- having --.

Column 20, line 2, Claim 19, "comprising" should be -- consisting of --.

Column 20, line 4, Claim 20, "comprising" should be -- having --.

UNITED STATES PATENT AND TRADEMARK OFFICE
CERTIFICATE OF CORRECTION

| | | |
|---|---|---|
| PATENT NO. | : 7,709,654 B2 | Page 1 of 1 |
| APPLICATION NO. | : 11/900329 | |
| DATED | : May 4, 2010 | |
| INVENTOR(S) | : Milton R. Smith, III et al. | |

It is certified that error appears in the above-identified patent and that said Letters Patent is hereby corrected as shown below:

In the Specification

In column 1, lines 15-17, please delete:

"This invention was supported by a grant from the National Institute of Health (NIH)—Grant No. GM063188. The U.S. Government has certain rights to this invention."

and insert:

-- This invention was made with government support under GM063188 awarded by the National Institutes of Health. The government has certain rights in the invention. --

Signed and Sealed this
Twenty-second Day of July, 2014

Michelle K. Lee
*Deputy Director of the United States Patent and Trademark Office*